(12) United States Patent
Tsay et al.

(10) Patent No.: US 8,657,759 B2
(45) Date of Patent: Feb. 25, 2014

(54) COMPARTMENTALIZED IMPLANT FITTING SOFTWARE

(75) Inventors: Ishan Ann Tsay, Highlands Ranch, CO (US); Christopher J. Long, Centennial, CO (US); Sean Lineaweaver, Parker, CO (US)

(73) Assignee: Cochlear Limited, Macquarie University, NSW (AU)

( * ) Notice: Subject to any disclaimer, the term of this patent is extended or adjusted under 35 U.S.C. 154(b) by 167 days.

(21) Appl. No.: 12/941,759

(22) Filed: Nov. 8, 2010

(65) Prior Publication Data
US 2012/0116480 A1    May 10, 2012

(51) Int. Cl.
*A61B 5/12* (2006.01)
(52) U.S. Cl.
USPC .................................. 600/559; 607/57
(58) Field of Classification Search
USPC ............................... 607/57; 600/559
See application file for complete search history.

(56) References Cited

U.S. PATENT DOCUMENTS

| | | | |
|---|---|---|---|
| 4,532,930 | A | 8/1985 | Crosby et al. |
| 4,953,112 | A | 8/1990 | Widin et al. |
| 5,277,694 | A | 1/1994 | Leysieffer et al. |
| 6,157,861 | A | 12/2000 | Faltys et al. |
| 6,322,521 | B1 | 11/2001 | Hou |
| 6,697,674 | B2 | 2/2004 | Leysieffer |
| 7,181,297 | B1 | 2/2007 | Pluvinage et al. |
| 7,343,021 | B2 | 3/2008 | Takagi et al. |
| 2003/0133578 | A1 | 7/2003 | Durant |
| 2004/0019464 | A1 | 1/2004 | Martucci et al. |
| 2005/0107845 | A1* | 5/2005 | Wakefield et al. ............ 607/57 |
| 2006/0235332 | A1 | 10/2006 | Smoorenburg |
| 2007/0255343 | A1* | 11/2007 | McMahon et al. ............ 607/54 |
| 2008/0033507 | A1* | 2/2008 | Litvak et al. .................. 607/57 |
| 2008/0222042 | A1 | 9/2008 | Moore et al. |
| 2010/0145411 | A1* | 6/2010 | Spitzer .......................... 607/57 |
| 2010/0152813 | A1* | 6/2010 | Lineaweaver et al. ........ 607/57 |
| 2010/0268302 | A1 | 10/2010 | Botros |

OTHER PUBLICATIONS

Forrest, Stephanie, "Genetic Algorithms: Principles of Natural Selection Applied to Computation", Science, Aug. 13, 1993, vol. 261 (5123), Aug. 13, 1993, pp. 872-878.
International Search Report for PCT/US04/07400 mailed Aug. 27, 2004.
McElveen, et al., "Remote Programming of Cochlear Implants: A Telecommunications Model", Otology & Neurotology 2010, pp. 1-6.

(Continued)

*Primary Examiner* — Christopher D Koharski
*Assistant Examiner* — Michael Carey
(74) *Attorney, Agent, or Firm* — Kilpatrick, Townsend & Stockton, LLP.

(57) ABSTRACT

A compartmentalized fitting system that may be used by a recipient to determine device parameters, such as threshold and/or maximum comfort levels, for a stimulating medical device is provided. The compartmentalized fitting system segregates the fitting procedure into separate sessions. For example, in an embodiment, the fitting system provides a clinician driven setup session whereby a clinician may specify parameters that are to be used in fitting the medical device. After which, the fitting system may enter a recipient driven fitting session that is used to determine one or device parameters for the stimulating medical device. Once determined, the fitting system passes control to a clinician driven approval session whereby the clinician can approve the determined set of device parameters; and, if approved store the determined device parameters. This storage may comprise loading the determined device parameters onto the stimulating medical device for subsequent use by the device.

27 Claims, 14 Drawing Sheets

(56) References Cited

OTHER PUBLICATIONS

Ramos, et al., "Use of telemedicine in the remote programming of cochlear implants", Acta Oto-Laryngologica 2009, pp. 533-540.

Takagi, Hideyuki, "Interactive Evolutionary Computation: Fusion of the Capabilities of EC Optimization and Human Evaluation", Proceedings of the IEEE, Sep. 2001, vol. 89, No. 9, Aug. 1, 2001, pp. 1275-1296.

Wesarg, et al., "Remote Fitting in Nucleus cochlear implant recipients", Acta Oto-Laryngologica, Apr. 19, 2010, pp. 1-10.

Written Opinion for PCT/US04/07400 dated Aug. 27, 2004.

International Search Report for International Application No. PCT/IB2011/054986 mailed May 3, 2012 (3 pages).

Written Opinion for International Application No. PCT/IB2011/054986 mailed May 3, 2012 (5 pages).

* cited by examiner

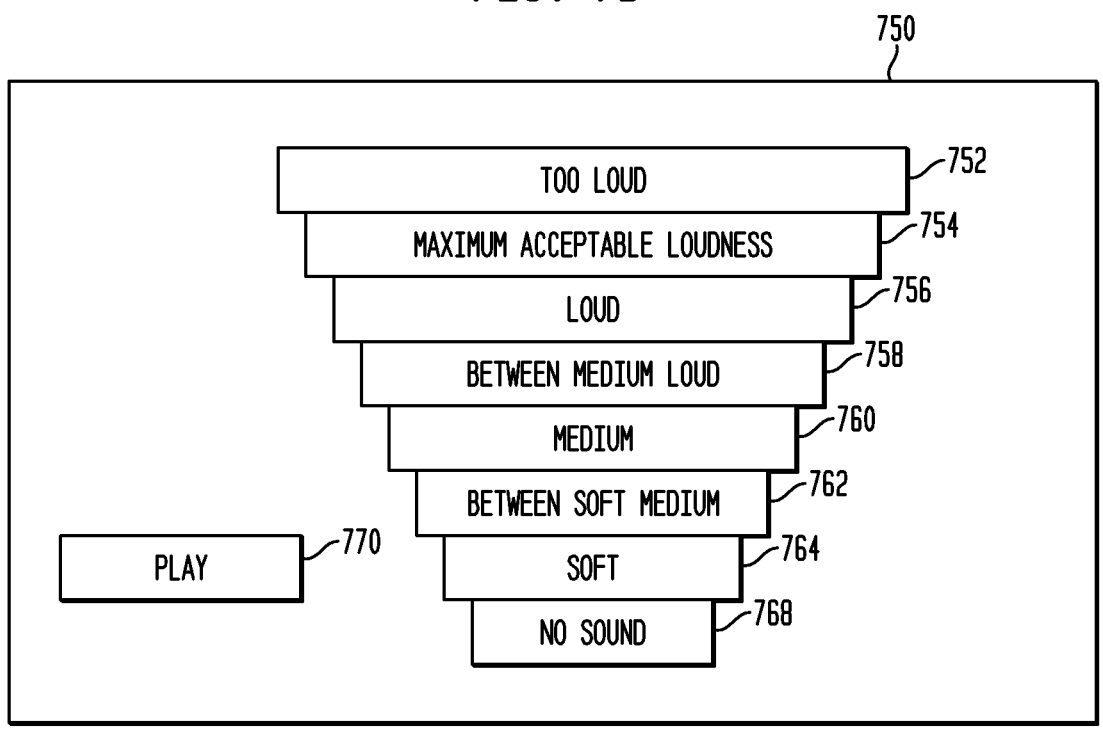

FIG. 10A

User Create Maps | Load By GA Search Space

Manually add maps that will be created by MyMaps

Create Maps

Stimulation Rate: 500

Maxima: 4

☑ Enable ADRO

[Add Map] [Remove Map]

MAPs that will be created:

| Number | ADRO Enabled | Stimulation Rate | Number of maxima |
|---|---|---|---|
| | | | |

| Use during session | Number | Title | ADRO Enabled | Stimulation Rate | Number of maxima |
|---|---|---|---|---|---|
| ☐ | 2 | stomSound2 | True | 500 | 8 |
| ☐ | 3 | MyMaps | False | 500 | 10 |
| ☐ | 3 | MyMaps | False | 900 | 10 |
| ☐ | 3 | MyMaps | False | 900 | 10 |
| ☐ | 4 | MyMaps | False | 900 | 10 |
| ☐ | 5 | MyMaps | False | 500 | 10 |
| ☐ | 5 | MyMaps | False | 500 | 8 |
| ☐ | 6 | MyMaps | False | 500 | 10 |
| ☐ | 7 | MyMaps | False | 500 | 10 |
| ☐ | 8 | MyMaps | False | 900 | 10 |

FIG. 10B

| | | | | | |
|---|---|---|---|---|---|
| User Creat Maps | Load By GA Search Space | | | | |

Show maps required by GA Search Space. MyMaps will create the missing maps.

Search Space: C:\Documents and Settings\XXXX\My Documents\XXXXXXXXXXXXXXXXXXXX

MAPs required by GA Search

| ADRO Enabled | Stimulation Rate | Number of maxima |
|---|---|---|
| false | 500 | 10 |
| false | 500 | 8 |
| false | 500 | 6 |
| false | 500 | 20 |
| false | 900 | 16 |
| false | 500 | 16 |

| Use during session | Number | Title | ADRO Enabled | Stimulation Rate | Number of maxima |
|---|---|---|---|---|---|
| ☐ | | | | | |
| ☐ | 2 | stomSound2 | True | 500 | 8 |
| ☐ | 3 | MyMaps | False | 500 | 10 |
| ☐ | 3 | MyMaps | False | 900 | 10 |
| ☐ | 3 | MyMaps | False | 900 | 10 |
| ☐ | 4 | MyMaps | False | 900 | 10 |
| ☐ | 5 | MyMaps | False | 500 | 10 |
| ☐ | 5 | MyMaps | False | 500 | 8 |
| ☐ | 6 | MyMaps | False | 500 | 10 |
| ☐ | 7 | MyMaps | False | 500 | 10 |
| ☐ | 8 | MyMaps | False | 900 | 10 |

COMPARTMENTALIZED IMPLANT FITTING SOFTWARE

RELATED APPLICATIONS

This application is related to U.S. patent application Ser. No. 12/557,242, entitled "Determining Stimulation Level Parameters in Implant Fitting," filed Sep. 10, 2009, and U.S. patent application Ser. No. 12/879,727 entitled "Determining Stimulation Level Parameters in Implant Fitting," filed Sep. 10, 2010, the entire contents and disclosures which are hereby incorporated by reference.

BACKGROUND

1. Field of the Invention

The present invention relates generally to stimulating medical devices, and more particularly, to fitting a stimulating medical device.

2. Related Art

Hearing loss, which may be due to many different causes, is generally of two types, conductive and sensorineural. In some cases, a person may have hearing loss of both types. Conductive hearing loss occurs when the normal mechanical pathways for sound to reach the cochlea, and thus the sensory hair cells therein, are impeded, for example, by damage to the ossicles. Conductive hearing loss is often addressed with conventional hearing aids which amplify sound so that acoustic information can reach the cochlea.

In many people who are profoundly deaf, however, the reason for their deafness is sensorineural hearing loss. Sensorineural hearing loss occurs when there is damage to the inner ear or to the nerve pathways from the inner ear to the brain. Those suffering from some forms of sensorineural hearing loss are unable to derive suitable benefit from conventional hearing aids. As a result, hearing prostheses that deliver electrical stimulation to nerve cells of the recipient's auditory system have been developed to provide the sensations of hearing to persons whom do not derive adequate benefit from conventional hearing aids. Such stimulating hearing prostheses include, for example, auditory brain stimulators and cochlear prostheses (commonly referred to as cochlear prosthetic devices, cochlear implants, cochlear devices, and the like; simply "cochlear implants" herein.) As used herein, the recipient's auditory system includes all sensory system components used to perceive a sound signal, such as hearing sensation receptors, neural pathways, including the auditory nerve and spiral ganglia, and regions of the brain that sense sound.

Sensorineural hearing loss is commonly due to the absence or destruction of the cochlear hair cells which transduce acoustic signals into nerve impulses. Cochlear implants help treat such sensorial hearing loss. Cochlear implants use direct electrical stimulation of auditory nerve cells to bypass absent or defective hair cells that normally transduce acoustic vibrations into neural activity. Such devices generally use an electrode array implanted into the scala tympani of the cochlea so that the electrodes may differentially activate auditory neurons that normally encode differential pitches of sound.

Auditory brain stimulators are used to treat a smaller number of recipients with bilateral degeneration of the auditory nerve. For such recipients, the auditory brain stimulator provides stimulation of the cochlear nucleus in the brainstem.

SUMMARY

In one aspect of the present invention there is provided a method for fitting a stimulating medical device to a recipient, comprising: executing a recipient driven fitting session for determining values for a set of one or more device parameters for the stimulating medical device; presenting the determined set of parameter values to a clinician; receiving an indication from the clinician that the determined set of parameter values are approved; receiving authentication information from the clinician; authenticating the clinician by determining if the received authentication information matches stored authentication information for the clinician; and storing the determined set of device parameter values, if approved by said clinician and said clinician is authenticated.

In another aspect of the present invention there is provided a system for fitting a stimulating medical device to a recipient, comprising: a fitting system controller configured to transmit a signal to cause the stimulating medical device to apply stimulation to the recipient; a display configured to display a graphical user interface to the recipient; and an input device configured to receive a response from the recipient, using the graphical user interface, regarding stimulation applied by the stimulating medical device; wherein the fitting system controller is further configured to determine a value for a set of at least one device parameter using the received response, present the determined set of parameter values to a clinician; receive an indication from the clinician that the determined set of parameter values are approved; receive authentication information from the clinician; authenticate the clinician by determining if the received authentication information matches stored authentication information for the clinician; and store the determined set of device parameter values, if approved by said clinician and said clinician is authenticated.

In yet another aspect of the present invention there is provided a system for fitting a stimulating medical device to a recipient, comprising: means for executing a recipient driven fitting session for determining values for a set of one or more device parameters for the stimulating medical device; means for presenting the determined set of parameter values to a clinician; means for receiving an indication from the clinician that the determined set of parameter values are approved; means for receiving authentication information from the clinician; means for authenticating the clinician by determining if the received authentication information matches stored authentication information for the clinician; and means for storing the determined set of device parameter values, if approved by said clinician and said clinician is authenticated.

BRIEF DESCRIPTION OF THE DRAWINGS

Embodiments of the present invention are described below with reference to the attached drawings, in which:

FIG. 7B illustrates another exemplary GUI that may be provided to a recipient for measuring comfort levels, in accordance with an embodiment;

FIGS. 10A-10B illustrates an exemplary clinical graphical user interface that may used to add a MAP for level (e.g., T and C) measurement, in accordance with an embodiment;

DETAILED DESCRIPTION

Aspects of the present invention are generally directed to a compartmentalized fitting system that may be used by a recipient to determine device parameters for a stimulating medical device. The compartmentalized fitting system segregates the fitting procedure into separate sessions. For example, in an embodiment, the fitting system provides a clinician driven setup session whereby a clinician may specify parameters that are to be used in fitting the medical device. After which, the fitting system may enter a recipient driven fitting session that is used to determine one or device parameters for the stimulating medical device. Once determined, the fitting system passes control to a clinician driven approval session whereby the clinician can approve the determined set of device parameters; and, if approved load the determined device parameters onto the stimulating medical device for subsequent use by the device.

Embodiments of the present invention are described herein primarily in connection with one type of hearing prosthesis, namely a cochlear prostheses (commonly referred to as a cochlear prosthetic devices, cochlear implant, cochlear devices, and the like; simply "cochlea implant" herein.) Cochlear implants generally refer to hearing prostheses that deliver electrical stimulation to the cochlea of a recipient. As used herein, cochlear implants also include hearing prostheses that deliver electrical stimulation in combination with other types of stimulation, such as acoustic or mechanical stimulation. It would be appreciated that embodiments of the present invention may be implemented in any cochlear implant or other hearing prosthesis now known or later developed, including auditory brain stimulators, or implantable hearing prostheses that acoustically or mechanically stimulate components of the recipient's middle or inner ear.

Figure 1:
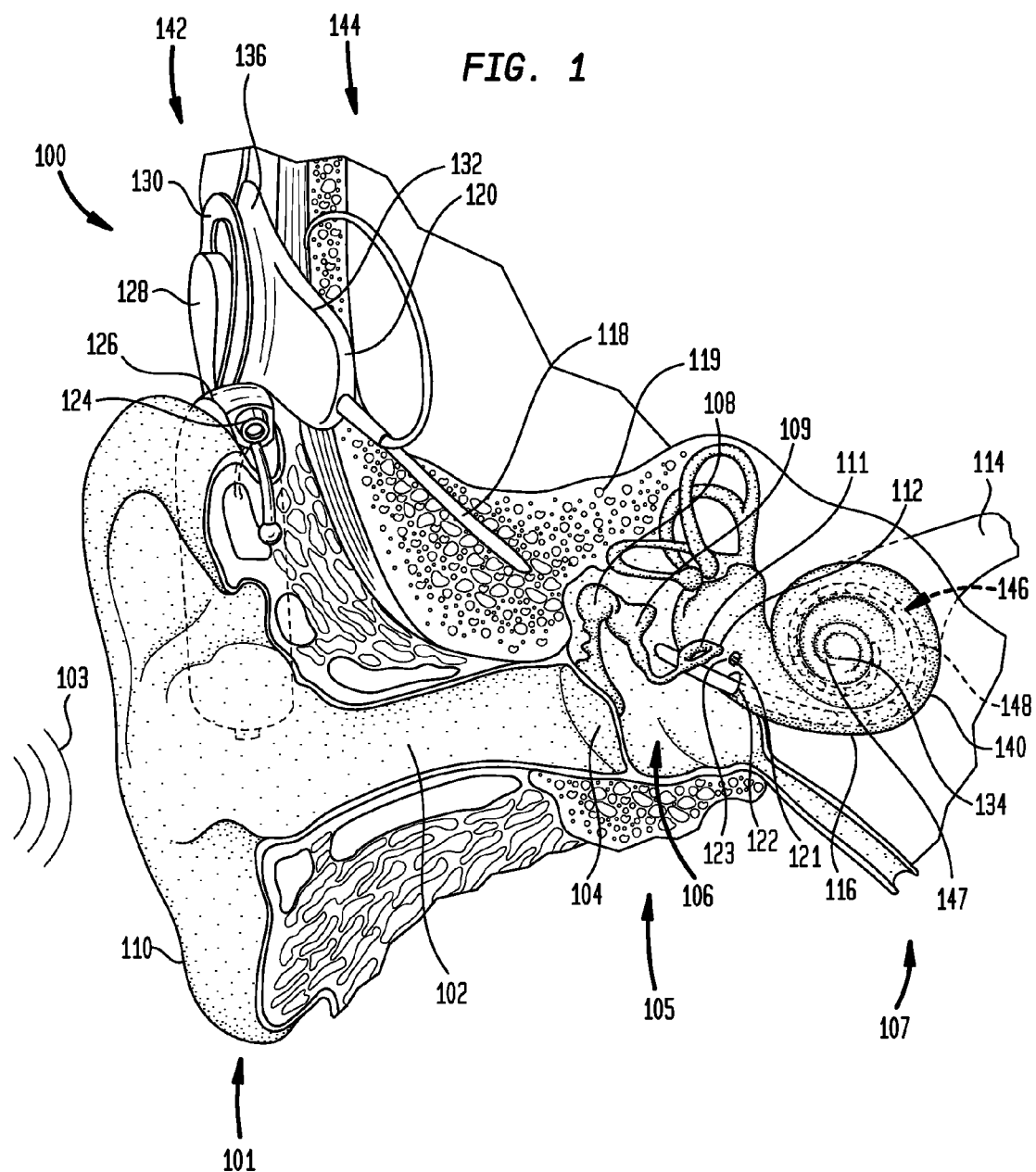
FIG. 1 is a perspective view of a cochlear implant in which embodiments of the present invention may be implemented.

FIG. 1 is perspective view of a conventional cochlear implant, referred to as cochlear implant 100 implanted in a recipient having an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

Cochlear implant 100 comprises an external component 142 which is directly or indirectly attached to the body of the recipient, and an internal component 144 which is temporarily or permanently implanted in the recipient. External component 142 typically comprises one or more sound input elements, such as microphone 124 for detecting sound, a sound processing unit 126 (also referred to herein as sound processor 126), a power source (not shown), and an external transmitter unit 128. External transmitter unit 128 comprises an external coil 130 and, preferably, a magnet (not shown) secured directly or indirectly to external coil 130. Sound processing unit 126 processes the output of microphone 124 that is positioned, in the depicted embodiment, by auricle 110 of the recipient. Sound processing unit 126 generates encoded signals, sometimes referred to herein as encoded data signals, which are provided to external transmitter unit 128 via a cable (not shown).

Internal component 144 comprises an internal receiver unit 132, a stimulator unit 120, and an elongate electrode assembly 118. Internal receiver unit 132 comprises an internal coil 136, and preferably, a magnet (also not shown) fixed relative to the internal coil. Internal receiver unit 132 and stimulator unit 120 are hermetically sealed within a biocompatible housing, sometimes collectively referred to as a stimulator/receiver unit. The internal coil receives power and stimulation data from external coil 130, as noted above. Elongate electrode assembly 118 has a proximal end connected to stimulator unit 120, and a distal end implanted in cochlea 140. Electrode assembly 118 extends from stimulator unit 120 to cochlea 140 through mastoid bone 119, and is implanted into cochlea 104. In some embodiments electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrodes 148, sometimes referred to as electrode array 146 herein, disposed along a length thereof Although electrode array 146 may be disposed on electrode assembly 118, in most practical applications, electrode array 146 is integrated into electrode assembly 118. As such, electrode array 146 is referred to herein as being disposed in electrode assembly 118. Stimulator unit 120 generates stimulation signals which are applied by electrodes 148 to cochlea 140, thereby stimulating auditory nerve 114.

In cochlear implant 100, external coil 130 transmits electrical signals (i.e., power and stimulation data) to internal coil 136 via a radio frequency (RF) link. Internal coil 136 is typically a wire antenna coil comprised of multiple turns of electrically insulated single-strand or multi-strand platinum or gold wire. The electrical insulation of internal coil 136 is provided by a flexible silicone molding (not shown). In use, implantable receiver unit 132 may be positioned in a recess of the temporal bone adjacent auricle 110 of the recipient.

The sound processing unit 126 may store a set of parameters that the sound processing unit 126 uses in processing sound to generate the encoded signals specifying the stimulation signals to be applied by electrodes 148. This set of parameters and their respective values is collectively and generally referred to herein as a "parameter map," a "cochlear map" or "MAP." A "MAP" is also sometimes referred to as a "program."

When a recipient first receives a cochlear implant 100, the system 100 is fitted or adjusted to the recipient since each recipient experiences different sound perceptions. It is noted that fitting may also be periodically performed during the operational use of the cochlear implant system 100. As used herein the terms "fit," "adjust," "program," "fitting," "adjusting," "mapping," or "programming," relate to determining one or more device parameters for a device. These device parameters may include parameters resulting in electronic or software programming changes to the stimulating medical device. The particular device parameters determined during the fitting session may vary depending on the multimodal hearing system. In the cochlear implant of FIG. 1, the device parameters may include one or more of the MAP parameters. These MAP parameters may include, for example, the number of channels, T-levels, C-levels, gain, frequency of stimulation, compression characteristic, type of strategy, number of maxima, etc.

Typically fitting is performed with a specialist, i.e. a hearing clinician, who adjusts parameters to ensure that the cochlear implant system performs as intended for that particular recipient. As will be discussed in more detail below, an exemplary embodiment supports a recipient driven fitting session where a recipient directly interacts with a computer system to determine at least one of parameter MAP values. In accordance with this embodiment, a clinician exercises oversight of the fitting process by permitting a clinician to set up the recipient driven fitting session, turn control over to the recipient for performing the fitting session, and then approve of determined parameters prior subsequent use by the stimulating medical device.

Figure 2:
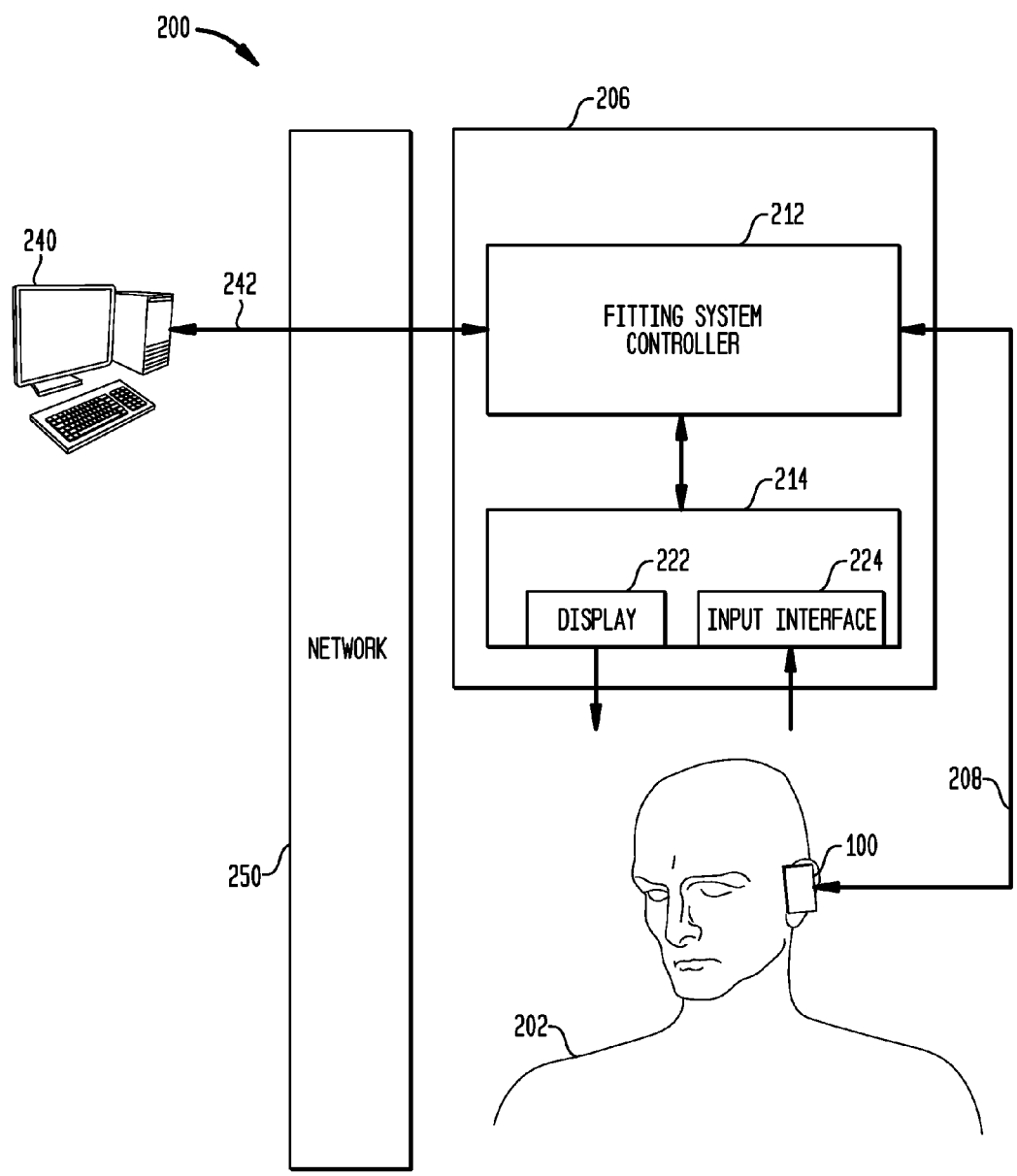
FIG. 2 is a schematic diagram illustrating one exemplary fitting system for determining device parameters for a stimulating medical device, in accordance with an embodiment.

FIG. 2 is a schematic diagram illustrating one exemplary fitting system 200 for determining device parameters for a stimulating medical device 100, in accordance with an embodiment. As used herein, the term "device parameter" refers to parameter(s) for the stimulating medical device 100 determined during the recipient driven fitting session. In the embodiment illustrated in FIG. 2, sound processing unit 126 of cochlear implant 100 may be connected directly to fitting system 206 to establish a data communication link 208 between the sound processing unit 126 and fitting system 206. Fitting system 206 is thereafter bi-directionally coupled by means of data communication link 208 with sound processing unit 126. It should be appreciated that although sound processing unit 126 and fitting system 206 are connected via a cable in FIG. 2, any communications link now or later developed may be utilized to communicably couple the implant and fitting system.

Fitting system 206 may further be connected over a communication link 242 to a clinician console 240 via a network 250. In the illustrated embodiment, clinician console 240 may be, for example, a standard personal computer. However, it should be understood that in other embodiments the clinician computer 240 may a personal digital assistant (PDA), a special purpose device, or any other suitable device for enabling a clinician to communicate with fitting system 206. Network 250 may be any combination of local and/or wide area network(s). For example, in an embodiment, network 250 may comprise Ethernet based local area networks (LAN) connected directly to the clinician console 240 and fitting system 206, respectively, and each LAN connected via a Wide Area Network (WAN) such as the Internet.

Fitting system 206 may comprise a fitting system controller 212 as well as a user interface 214. Controller 212 may be any type of device capable of executing instructions such as, for example, a general or special purpose computer, digital electronic circuitry, integrated circuitry, specially designed ASICs (application specific integrated circuits), firmware, software, and/or combinations thereof User interface 214 may comprise a display 222 and an input interface 224. Display 222 may be, for example, any type of display device, such as, for example, those commonly used with computer systems. Input interface 224 may be any type of interface capable of receiving information from a recipient, such as, for example, a computer keyboard, mouse, voice-responsive software, touch-screen (e.g., integrated with display 222), retinal control, joystick, and any other data entry or data presentation formats now or later developed.

Clinician console 240 and fitting system controller 212 may execute software that enables clinician console 240 to exercise control over fitting system controller 212. For example, in an embodiment, clinician console 240 and fitting system controller 212 may execute a remote desktop software package, such as GoToMyPC, that enables a clinician via clinician console 240 to connect to and exercise control over fitting system controller 212. A more detailed description of an exemplary mechanism for a clinician exercising control over fitting system controller 212 will be discussed below. Further, it should be understood that although the presently discussed embodiment is discussed with reference to a clinician remotely connecting to fitting system controller 212, in other embodiments, the clinician may be co-located with the recipient. A further description of an embodiment in which the clinician is co-located with the recipient will be presented below with reference to FIG. 11.

Figure 3:
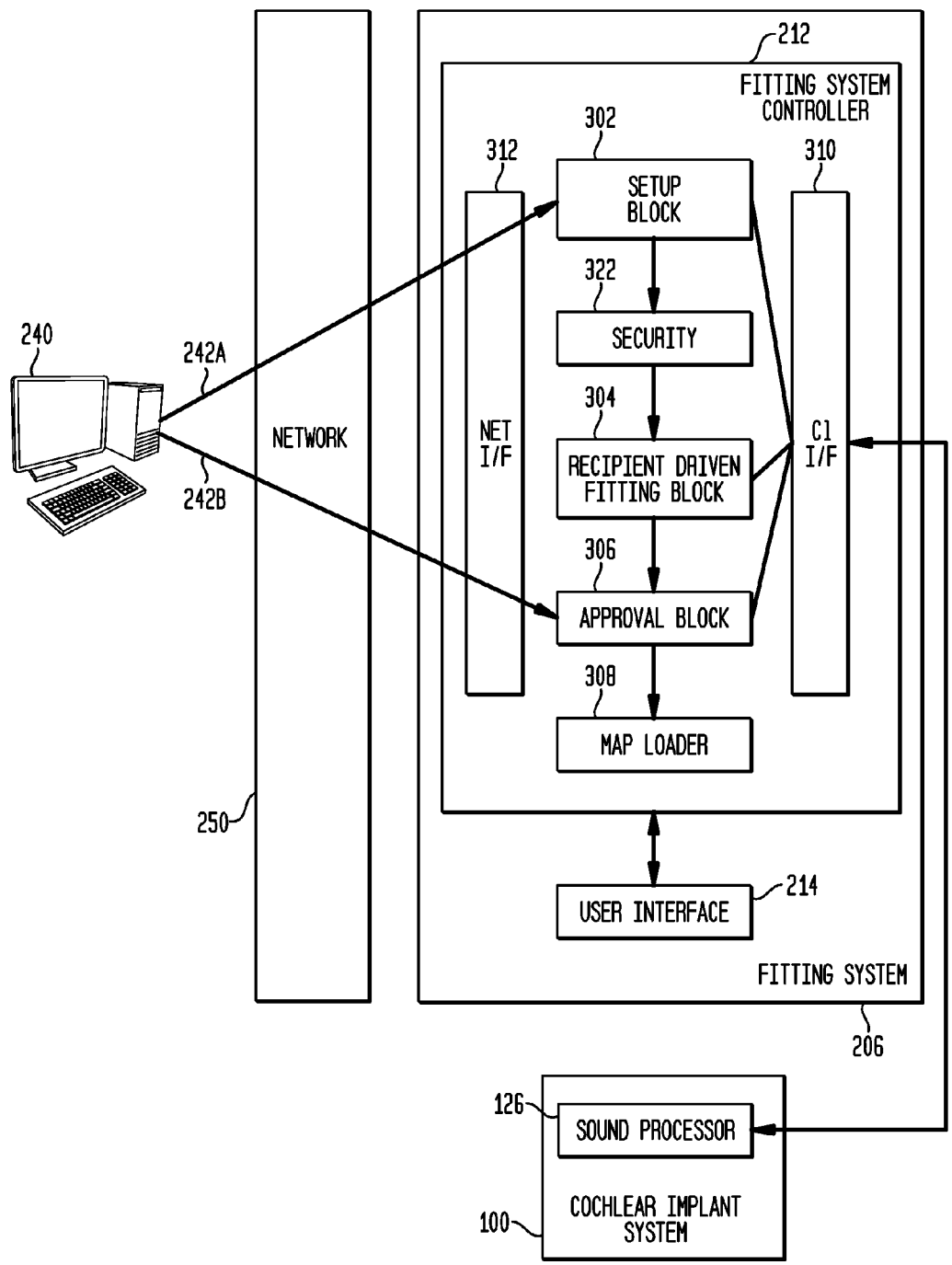
FIG. 3 provides a functional block diagram of the fitting system of FIG. 2, in accordance with an embodiment.

FIG. 3 provides a functional block diagram of the fitting system of FIG. 2, in accordance with an embodiment. As illustrated fitting system controller 212 may include a setup session block 302, a recipient driven fitting session block 304, an clinician approval block 306 and map loader block 308, a security block 322 between the setup session block 302 and the recipient driven fitting session block 304, and a security block 324 between the recipient driven fitting block 304 and the approval and map loader block 306. Further, as shown, fitting system controller 312 may include a network interface 312 that enables the fitting system controller 312 to communicate over network 250. Fitting system controller 312 further includes a cochlear implant (CI) interface that enables fitting system controller 312 to communicate with sound processor 126 of cochlear implant 100. Each of these functional blocks may be software blocks executed by one or more processors of the fitting system controller 212.

Figure 4:
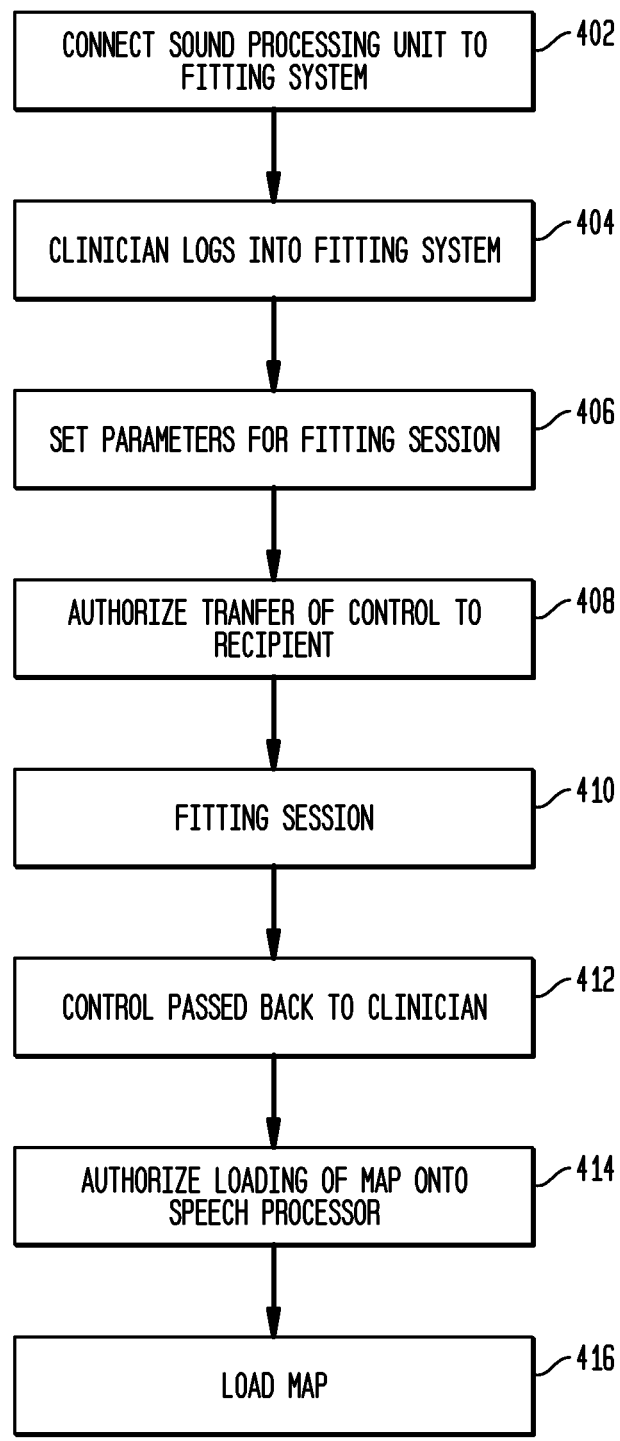
FIG. 4 provides a flow chart of an exemplary method for fitting a stimulating medical device, in accordance with an embodiment of the present invention.

FIG. 4 provides a flow chart of an exemplary method for fitting a stimulating medical device, in accordance with an embodiment of the present invention. FIG. 4 will be discussed with reference to the above-discussed FIG. 3. Further, in this exemplary description, the recipient driven fitting session will involve the recipient determining stimulation level parameters for the cochlear implant 100. That is, in this example, the determined device parameters are stimulation parameters. As noted above, the term device parameter refers to a parameter for a device determined during a recipient driven fitting session. As used herein, "a stimulation level parameter" refers to any parameter regarding a stimulation level, such as, for example, threshold levels and/or maximum comfort levels for a stimulating medical device. For example, in an embodiment, the fitting system 206 may be used by the recipient 202 to determine the thresholds and maximum comfort levels, T-levels and C-levels, respectively, for each electrode contact 148 of stimulating lead assembly 118. Further, these T-levels and C-levels may be determined for a set of possible MAPs that may be used by a genetic algorithm subsequently used in fitting the cochlear implant 100.

It should be noted that although in the discussion of FIG. 4, the recipient driven fitting session involves determining the T and C-levels for a plurality of MAPs, in other embodiments the recipient driven fitting session may involve a different process for determining one or more parameters for the cochlear implant 100.

A recipient 202 or clinician may initiate the process by connecting cochlear implant 100 to fitting system 206 at block 302. This may be accomplished by plugging a cable into the sound processor 126 of the cochlear implant 100 and the fitting system 206. Or, for example, fitting system 206 and cochlear implant 100 may connect wirelessly in response to, for example, the recipient or a clinician entering an instruction (e.g., via user interface 214 or clinician console 240) that instructs fitting system 206 to wirelessly initiate a connection with cochlear implant 100. This connection may also cause the fitting system to begin some initialization procedures. These initialization procedures may include a calibration step to help ensure that constant sound level pressure is delivered to the sound processing unit 126 of the cochlear implant 100 by the fitting system 206.

A clinician connects clinician console 240 to fitting system controller 212 at block 404. For example, clinician console 240 may execute software, such as remote desktop software (e.g., GotoMyPC, PCAnywhere, etc.) to establish a communications link 242A to remotely access the fitting system controller 212. This software may enable the clinician to view the information displayed by display 222 of fitting system 206. Once connected to fitting system controller 212, the clinician may direct the fitting system controller 212 to execute fitting software stored by a storage device (e.g., hard drive, flash memory, etc.).

The fitting software executed by the fitting system controller 212 may then display a screen directing the clinician to enter authentication information that is used to verify that the clinician is authorized to access setup session block 302. This authentication information may comprise a user name and password for the clinician. Using authentication information, such as a user name and password, helps ensure that the recipient 202 does not perform the fitting process without clinician approval.

Once the clinician correctly enters their authentication information, the fitting system controller 212 may enter a setup session block 302. This setup session block 302 enables the clinician to specify the one or more parameters for use by the fitting system controller 212 in fitting the cochlear implant 100 to the recipient 202. Parameters specified by the clinician for use by the recipient driven fitting session are referred to herein as fitting parameters. These fitting parameters may include algorithm parameters and MAP parameters. The algorithm parameters specify how the fitting process is to be performed. For example, algorithm parameters may include parameters specifying a current level step size, a number of reversals to be used, the duration of sounds (e.g., beeps to be played), the number of beeps, the type of sounds, an interpolation algorithm (e.g., a linear interpolation or non-linear interpolation algorithm), the sequence of operations to be performed, the specific fitting algorithm to use during the fitting session, etc. The MAP parameters may include MAP parameters such as discussed above. For example, the MAP parameters specified by the clinician may include a stimulation rate(s) and a number of maxima(s), a gain, compression characteristics, the type of signal processing strategy (e.g., ACE, PACE, etc.), etc. There are a myriad of mechanisms that fitting system controller 212 may use in enabling the clinician to enter the fitting parameters, such as, for example, drop down menus, fields to enter numbers or text, check boxes, buttons, etc. A further description of how these exemplary fitting parameters may be used during the fitting process will be provided below.

During execution of the setup session, the user interface 214 may be, for example, disabled so that the recipient does not modify the fitting parameters entered by the clinician. Additionally, in an embodiment, during the setup session, display 222 of user interface 214 may be blanked, display a corporate logo, display information indicating that the fitting session will commence shortly, etc.

Once the clinician has finished providing the fitting parameters, the clinician may enter a command indicating the clinician has finished. The fitting system controller 212 may use different techniques for enabling the clinician to identify that they have finished entering the fitting parameters. For example, fitting system controller 212 may display a button that a clinician may click on via a mouse to identify that they are finished entering the set up parameters.

Once the clinician identifies that the clinician has finished entering the fitting parameters, the fitting system controller 212 may perform a check to identify if there are any errors or irregularities in the provided set up parameters. If so, the procedure may be halted and the fitting system controller 212 may identify the error/irregularity to the clinician and provide the clinician with an opportunity to correct the error/irregularity.

If the error check identifies no irregularities or the clinician elects to proceed with the procedure with the identified irregularities, the fitting system controller 212, at block 408, may enter a security function 322. The security function 322 may direct the clinician to enter their authentication information (e.g., username and password). This security check may help ensure that the recipient directed fitting session does not begin until the clinician determines that it should begin, and thus help ensure that a recipient doesn't improperly start the fitting session or alter set-up parameters.

After the security check, control passes, at block 410, to the recipient driven fitting session functional block 304 for determining the device parameter(s). As noted above, the term device parameter refers to a parameter determined during the recipient driven fitting session. During this session, the fitting system controller 212 executes a fitting process for fitting the cochlear implant 100 in accordance with the set-up parameters set by the clinician. During the fitting session, the clinician console 240 may display information indicating the progress of the fitting session, such as a percentage of completion of the fitting session, a graphic (e.g., a bar or pie chart that has a percentage of it colored in a particular color based on the percentage of completion, etc.)

As previously noted, the fitting system controller 212 may direct the cochlear implant 100 to apply electrical stimulation to the recipient during the fitting session. In the presently described embodiment, the signals for generating this electrical stimulation are locally generated during this fitting session by the fitting system controller 212. As such, the commands specifying the electrical stimulation do not traverse network 250 (e.g., they are not sent from the clinician console 240 nor rely on any contemporaneous command from the clinician console 240). Thus, the reliable application of stimulation is not dependent on network reliability. For example, should network 250 experience heavy traffic resulting in the connection between clinician console 240 and fitting system 206 failing, the fitting session may still reliably take place.

In an exemplary embodiment, fitting session functional block 304 may comprise software and/or hardware for determining stimulation level parameters for a stimulating medical device. As used herein, "a stimulation level parameter" refers to any parameter regarding a stimulation level, such as, for example, threshold levels and/or maximum comfort levels for a stimulating medical device. For example, in an embodiment, the fitting session functional block 304 may be used by a recipient to determine the thresholds and maximum comfort levels for the possible MAPs that may be used by a genetic algorithm in fitting the stimulating medical device. A further description of an exemplary fitting session for determining stimulation level parameters will be discussed in more detail below with reference to FIG. 5.

It should, however, be noted that the fitting session functional block 304 may perform alternative fitting processes. For example, in another embodiment, the clinician may specify, during setup session 406, the MAP parameters for the cochlear implant 100 with the exception of the T and C-levels. The recipient driven fitting session in such an embodiment may then involve determining the T and C-levels for each stimulation channel (e.g., electrode contact 148). The determined MAP (i.e., the clinician specified parameters and the determined T and C-levels) may then be approved by the clinician and subsequently uploaded to the cochlear implant or further processing, as will be discussed in more detail below with regard to block 416.

Or, in yet another embodiment, the recipient driven fitting session may involve using a genetic algorithm to search for an optimum MAP for the recipient. For example, in an embodiment, the fitting session functional block 304 may include software and/or hardware for performing a recipient driven genetic algorithm search for a MAP for subsequent use by sound processor 126. A more detailed description of an exemplary method for fitting a cochlear implant using a genetic algorithm is provided in U.S. patent application Ser. No. 12/557,208 entitled "Using a Genetic Algorithm to Fit A Cochlear Implant System to a Patient,", filed Sep. 10, 2009, which is hereby incorporated by reference.

Or, in yet another embodiment, the recipient driven fitting session performed at block 410 may involve a process of determining an initial set of parameters (collectively referred to as an initial stimulation profile) for the cochlear implant 100 and then determining the another set of parameters by modifying the stimulation profile. In such an embodiment, the initial stimulation profile may be representative of the T-levels for the cochlear implant, and the other stimulation profile may be representative of the comfort levels. In such an embodiment, the T-levels may be measured during the parameter set-up block 406, and the C-levels determined during the fitting session. A more detailed description of methods for generating a second stimulation profile from a first stimulation profile is provided in U.S. patent application Ser. No. 12/809,579, entitled "Fitting a Cochlear Implant," filed Jun. 18, 2010, which is hereby incorporated by reference herein.

It should be understood that the above are merely some exemplary procedures that may be performed during the recipient driven fitting session at block 410 and in other embodiments, other recipient driven procedures for determining one or more parameters for a stimulating medical device may be performed.

After completion of the recipient driven fitting session, at block 412, control passes back to the clinician (using a security functional block 322) for approval of the parameters determined during the fitting session. For example, in FIG. 3, the recipient driven fitting session block 304 passes control to clinician approval functional block 306.

The authentication functional block clinician approval functional block 306 may then reestablish the communication link 242B to the clinician console 240, if, for example, the communication link 242A had been terminated (e.g., due to heavy network traffic). The clinician may then review the parameters determined during the fitting session via a clinician interface displayed on clinician console 240. If the determined parameters are acceptable, the clinician may, at block 414, instruct the fitting system controller 212 to storing the determined parameters. In order to ensure the clinician approves of the parameters prior to store the parameters, the authorization function 308 may request that the clinician enter their authentication information (e.g., user name and password).

In addition to approving the determined parameters, in an embodiment, the clinician interface may also enable the clinician to adjust the determined parameters. Then, once adjusted and approved by the clinician, the parameters may be stored.

Once approved, security block 324 passes control to a map loader 306 that stores the determined parameters. For example, in an embodiment in which the fitting session 410 determines the T- and C-levels for a plurality of MAPs, the fitting system controller 212 may stored the determined parameters in a storage within or connected to fitting system controller 212.

Or, if the determined parameters are a singular MAP for use by cochlear implant (e.g., when the fitting session 410 performs a genetic algorithm or other search such as noted above), the fitting system controller 212 may load the determined MAP onto sound processor 126 via cochlear implant (CI) interface 310 at block 416. Sound processor 126 then stores the MAP for subsequent use by cochlear implant 100 in providing stimulation to recipient 202.

Because in this exemplary embodiment, the clinician only has to setup the initial parameters for the fitting session and approve the final results, the clinician has the potential to concurrently oversee many recipient driven fitting sessions. For example, once a clinician sets up a first recipient's fitting session, the clinician can then setup a second recipient's fitting session, while the first recipient is engaged in recipient driven fitting session. Thus, the amount of time required by the clinician for each fitting may be reduced and the clinician can thus oversee a greater number of fitting sessions. During the respective fitting sessions for each of the recipients, the clinician console may display information (provided by the respective fitting system controller's) regarding the progress of each fitting session. This information may include a percentage of completion or a graphic indicative of the percentage of completion (e.g., a bar or pie chart, as noted above).

Figure 5:
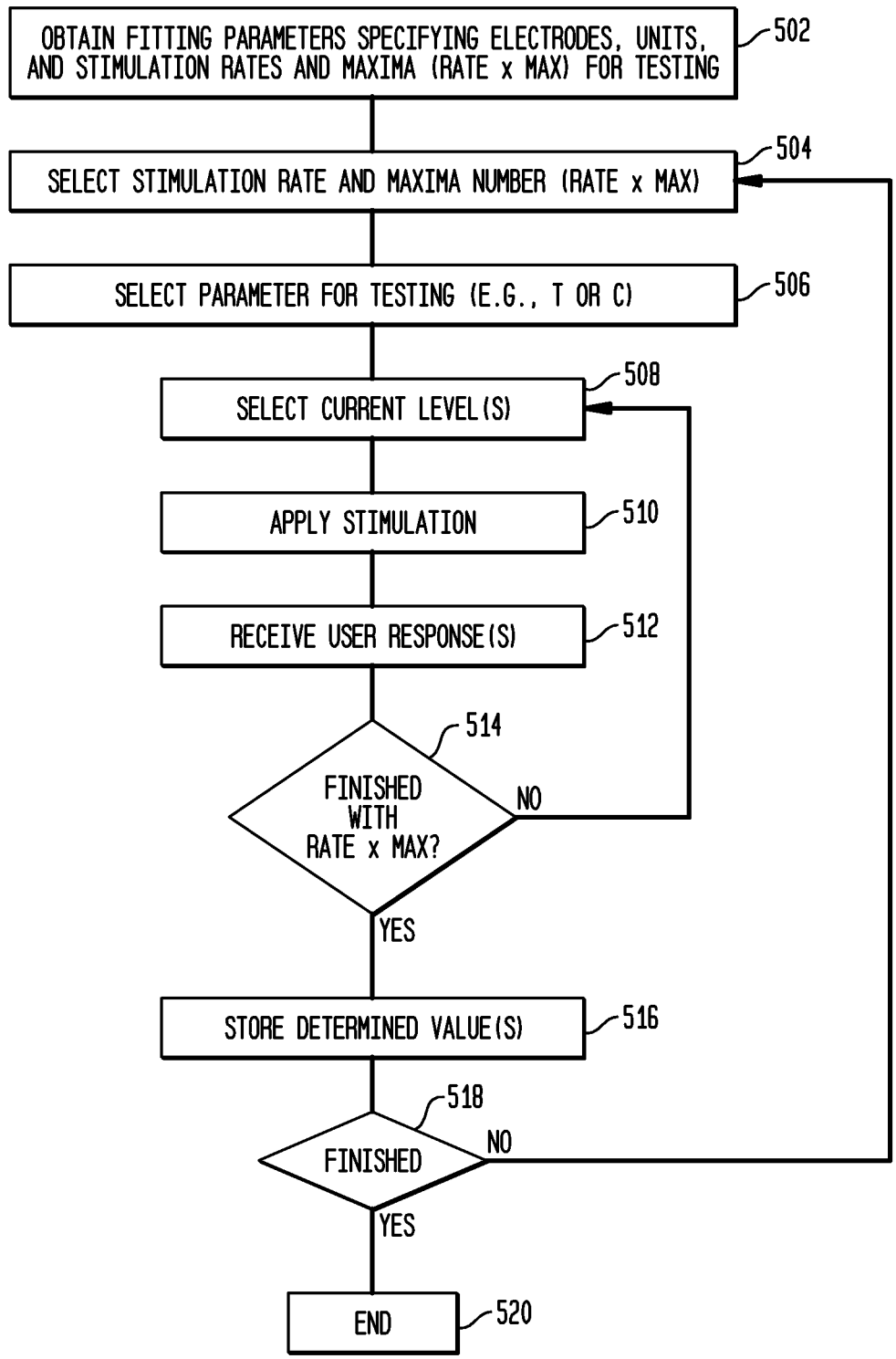
FIG. 5 is a high-level flow chart illustrating operations that may be performed for measuring parameters for a stimulating medical device, in accordance with an embodiment.

FIG. 5 provides an exemplary method that may be implemented by recipient driven fitting functional block 304 (hereinafter referred to as fitting function 304) in performing the fitting session at block 410. In this exemplary method, the fitting function 304 obtains the threshold and comfort levels for a plurality of different Rate×Max combinations. The Rate parameter represents the rate of stimulation, often referred to in units of pulses per second. And, the Max parameter represents the number of applied maxima with the MAP. These parameters (e.g., the Rate and Max parameters, and the Rate× Max combinations for which T- and C-levels are to be obtained) may be provided by the clinician at block 406.

It should be noted that FIG. 5 merely provides one example of a method for performing the fitting session of block 410, and that in other embodiments other methods may be performed. For example, as noted above, in embodiments, fitting session 410 may involve performing a genetic algorithm search to identify a particular MAP for subsequent use by the cochlear implant 100, or a procedure that simply determines the threshold and comfort levels for a MAP where all other MAP parameters are specified by the clinician at block 406, or an alternative procedure for determining one or more parameters for the cochlear implant 100.

Fitting function 304 may obtain the parameters for performing the desired measurements, at block 502. As noted above, these parameters may be provided by a clinician during block 406 and stored in a memory or other storage device of fitting system controller 212.

Fitting function 304 may then select a Rate×Max combination from amongst the combinations to be tested, at block 506. This initial Rate×Max combination may be specified by a parameter provided by the clinician at block 406, the fitting function 304 may randomly select one of the combinations, or any other mechanism may be used for selecting this initial combination.

Fitting function 304 may also select the parameter to be measured (e.g., T or C levels) at block 506. In other words, one of the fitting parameters specified by the clinician may include the parameter(s) to be measured during the recipient driven fitting session. Further, if more than one parameter is to be measured (e.g., both T and C levels), the fitting parameters specified by the clinician may include an algorithm parameter specifying the order in which the parameters are to be measured. Alternatively, the parameter(s) determined during the recipient driven fitting session and the order in which they are measured may be may be specified in an instruction set stored by the fitting controller system 212, or determined by the fitting function 304 in some other manner.

Fitting function 304 may then select one or more current level(s) for application of stimulation at block 508. Next, the fitting function 304 may direct the cochlear implant 100 to apply stimulation using the specified parameters and Rate× Max combination at block 510. The fitting function 304 may then obtain a recipient response at block 512 regarding the recipient's perception of the applied stimulation. This response may be provided by the recipient using input device 224. The fitting function 304 may then analyze the obtained response to determine at block 514 if additional testing is to be performed or not. If so, the fitting function 304 may store the received response at block 516 and return to block 508 for further testing.

There are various mechanisms that may be employed for selecting current levels (block 506), applying stimulation (block 508), and obtaining a recipient response (block 510). For example, in one embodiment, fitting function 304 may randomly select a number (e.g., a random number between 1 and 6) of stimulations to be applied in measuring threshold levels. Fitting function 304 may then select the current level for each of the stimulations. The fitting function 304 may then transmit information to the cochlear implant 100 to cause the cochlear implant to apply stimulation at each of the determined current levels. Each of these stimulations may be separated in time, such that if the recipient hears each of these stimulations, the recipient would hear a successive group of beeps each with a different loudness. In such an example, the recipient may be provided at block 512 with a GUI for entering their perception of the applied stimulation (e.g., how many beeps they heard). Exemplary GUIs and methods for obtaining parameter measurements using these exemplary GUIs are provided in more detail below with reference to FIGS. 7-9.

The fitting function 304 at block 518 may then determine if additional testing is to be performed. If so, the process returns to block 504. And, if not, the process ends at block 520. As noted above, the different tests to be performed may be stored in an instruction set or by fitting function 304. For example, during the first pass through the process, the fitting function 304 may measure the thresholds for one Rate×Max combination. Then, during a second pass through blocks 504 through 518, the comfort level for this Rate×Max combination may be measured. After which, the threshold and comfort levels for a different Rate×Max combination may be measured.

Figure 6:
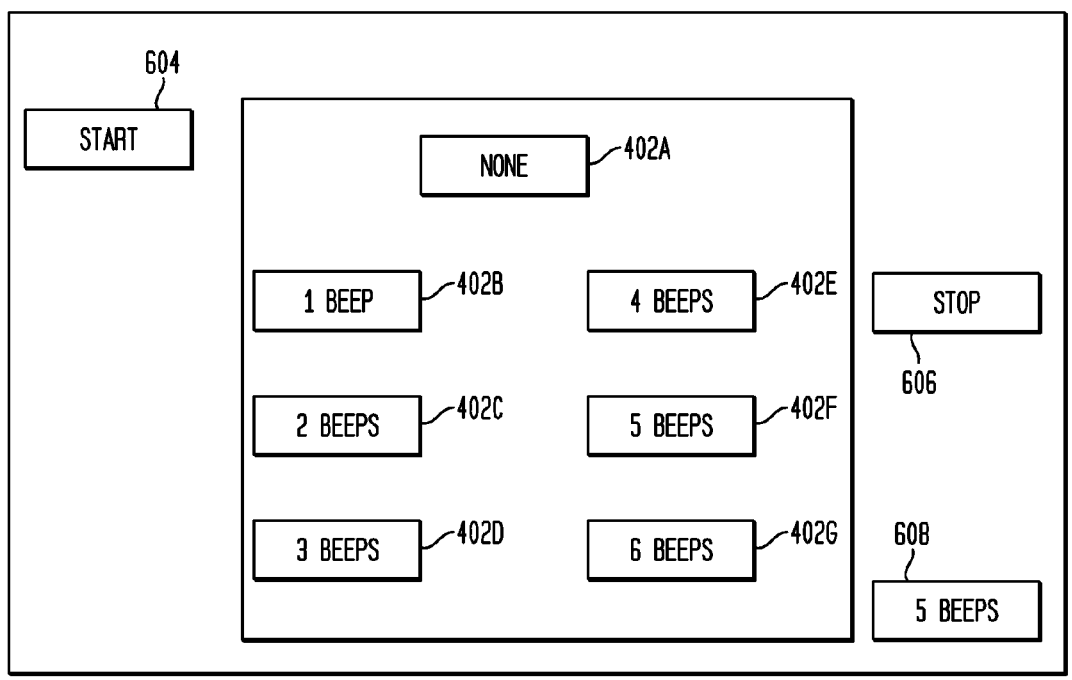
FIG. 6 illustrates an exemplary GUI that may be provided to a recipient for obtaining the recipients perception of applied stimulation, in accordance with an embodiment.

FIG. 6 illustrates an exemplary GUI 600 that may be provided to a recipient for obtaining the recipients perception of applied stimulation, in accordance with an embodiment. As illustrated, GUI 600 may comprise a set of icons 602 that the recipient may select to indicate how many beeps the recipient heard. For example, these icons 602 may include an icon for selecting that the recipient heard zero beeps 602A, one beep 602B, two beeps 602C, three beeps 602D, four beeps 602E, five beeps 602F, and six beeps 602G. This GUI 600 may be displayed on display 222. The recipient may, using input interface 224, select the icon corresponding to the number of beeps heard by the recipient. The input interface 224 may then provide this response to fitting system controller 212.

Additionally, GUI 600 may include a start icon 604 that the recipient may select to direct the fitting system controller 612 to start the application of stimulation. Additionally, the GUI 600 may comprise a stop button 606 that the recipient may select to stop the process, such as if the recipient needs to leave for any purpose. After the user enters their response GUI 600 may also display the correct number of beeps 608.

In response to an incorrect answer, the fitting system controller 212 may increase the current levels by one large step and apply the same number of stimulation signals at the increased current levels. In this manner, the current level quickly ascends to a general audible level (stimulation grows louder by large steps until sound is heard). In response to a correct answer, the fitting system controller 212 may drop the stimulation level to that which was previously inaudible and begin a counted-Ts procedure. The displayed GUI may remain the same throughout this process, and the question "How many beeps did you hear" continues. The counted-T's procedure refers herein to a procedure where the fitting system controller 212 randomly selects at block 508 a number of uniformly distributed beeps (e.g., between 2 and 6), rather than a fixed number. The recipient again chooses between the same buttons labeled "None", "1", "2", "3", "4", "5" and "6" 602A-G. In this way, thresholds may be measured more resolutely. With every correct response, the current level is decreased by 2 small steps, and with every incorrect response, the current level is increased by 1 small step at block 508. The task continues until the number of correct responses at any one level meets a particular value (named "Reversals") at block 514. This reversal value may be specified by the clinician using set-up functional block 302. Fitting function 304 may store the measured final threshold value at block 514. This threshold may be stored in a storage within fitting system controller 212.

After the thresholds for all electrodes to be measured of the cochlear implant 100 are determined, fitting system may check the determined values to see if there are any outliers. For example, threshold values typically follow a rather uniform curve across electrodes. If a measured threshold for a particular Rate×Max combination is found to be significantly above or below this curve, the fitting function 304 may then at block 514 re-measure the threshold for this or an adjacent electrode. This check may be performed, for example, by obtaining the median of all the computed thresholds and then determining if all the thresholds are within +/– a value (n) of the computed median.

Because the threshold values typically follow a rather uniform curve, in embodiments, the fitting system may measure thresholds for only a subset of the electrodes of the electrode array (e.g., 5 out of the 22 electrodes of the electrode array). The fitting system may then use these measured electrodes to interpolate the thresholds for the other electrodes. A further explanation of how thresholds may be interpolated by measuring the thresholds of a subset of the electrode array's electrodes is provided in U.S. patent application Ser. No. 10/518,812 entitled "Parametric Fitting of a Cochlear Implant," by Guido F. Smoorenburg and filed on Oct. 11, 2005, the entire contents of which are incorporated by reference herein. Or, for example, in an embodiment, the fitting system may use a "streamlined" fitting procedure in which linear interpolation is used (e.g., blind linear interpolation), rather than a curve-fitting technique based on heuristic (not blind) curves. One exemplary "streamlined" technique employing blind linear interpolation is provided in Plant et al., "Evaluation of Streamlined Programming Procedures for the Nucleus Cochlear Implant with the Contour Electrode Array," Ear and Hearing. 26(6):651-668, December 2005.

Figure 7A:
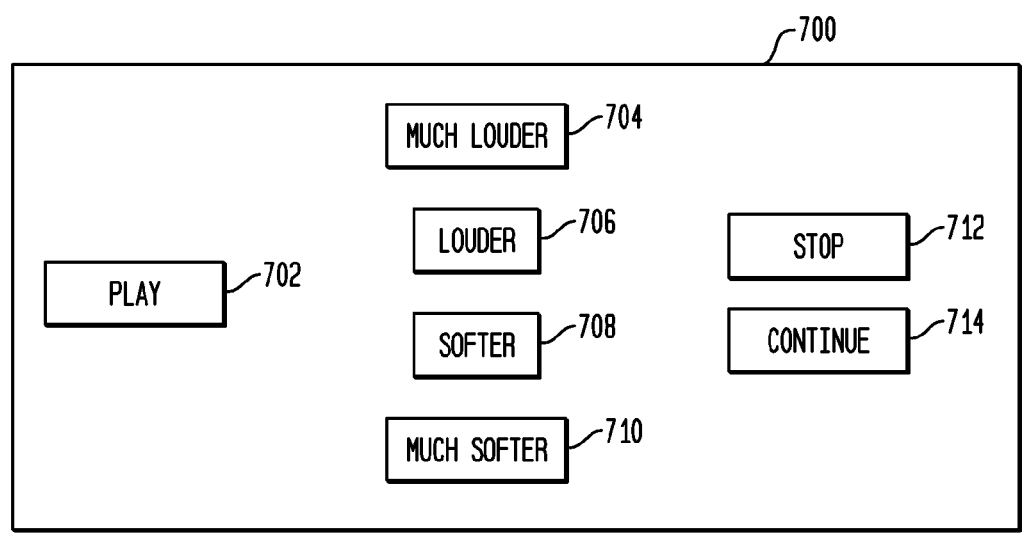
FIG. 7A illustrates an exemplary GUI that may be provided to a recipient for measuring comfort levels, in accordance with an embodiment.

As noted above, fitting function 304 may also be used to compute the comfort levels for each Rate×Max combination. FIG. 7A illustrates an exemplary GUI 700 that may be provided to a recipient for measuring the comfort levels, in accordance with an embodiment. As illustrated GUI 700 may include a play icon 702, a much louder icon 704, an louder icon 706, a softer icon 708, a much softer icon 710, a stop button 712, and a continue button 714. The play button 702 instructs the fitting function 304 to direct the cochlear implant 100 to apply stimulation using the currently specified T and C value, and the specified Rate×Max combination as well as the other parameters specified by the clinician at block 406. The louder button 706 increases the current level at block 508 by, for example, one step, and then the fitting function 304 at block 510 directs the cochlear implant 100 to apply stimulation at this new current level. The much louder button 704 functions in the same manner as louder button 706, but instead of increasing the current level by one step increases the current level by a larger increment (e.g., 2, 3, 4, etc. steps).

The softer button 708 decreases the current level at block 508 by for example, one step, and then the fitting function 304 at block 510 directs the cochlear implant 100 to apply stimulation at this new current level. The much softer button 710 functions in the same manner as softer button 708, but instead of decreasing the current level by one step increases the current level by a larger number of steps (e.g., 2, 3, 4, etc.). The step size as well as the number of step sizes each button may increase or decrease the current level may be specified in the instruction set obtained from the clinician at block 406. Further, in another example, the large step size may be individually specified and need not be a multiple of the small step size. Further, the step sizes for increasing and decreasing the current level may be the same or different.

The stop button 712 may cause the process to stop, such as, for example, if the recipient needs to leave or otherwise terminate the procedure. The continue button 714 may be used by the recipient to indicate that the maximum comfort level has been reached, and the process should continue to the next measurement at block 514.

This stimulation applied in accordance with GUI 700 may be representative of, for example, a beep at a particular frequency, a music clip, a person or people speaking, etc. Further, GUI 700 may be used to apply stimulation one electrode at a time to set the comfort levels one at a time. Or, for example, a stimulation signal in accordance with live audio may be applied and the current levels of all electrodes adjusted in response to the recipient's selection of one of the icons. This mechanism of using simulated live audio and adjusting the current levels of multiple electrodes simultaneously in response to the recipient's selection may use principals such as those discussed in U.S. patent application Ser. No. 10/518,812 entitled "Parametric Fitting of a Cochlear Implant," filed on Oct. 11, 2005, which is hereby incorporated herein in its entirety. For example, an initial current level profile may be determined based on the measured threshold levels. These measured threshold levels may be used to fit a curve. Then this curve may be adjusted up or down, or tilted in response to the recipient's selections to obtain the comfort levels.

It should be noted that GUI 700 is but one example of a user interface that may be presented to a recipient for measuring the maximum comfort levels for the recipient. FIG. 7B illustrates another exemplary GUI 750 comprising a different set of icons may be used for measuring the maximum comfort levels. As illustrated, GUI 750 displays a plurality of icons such as icons: Too Loud 752, Maximum Acceptable Loudness 754, Loud 756, Between Medium and Loud 758, Medium 760, Between Soft Medium 762, Soft 764, and No Sound 766. As with GUI 700, the stimulation applied may be representative of, for example, a beep at a particular frequency, a music clip, a person or people speaking, live sound arriving through the microphone of the cochlear implant, etc.

The stimulation may be applied at a particular current level and the recipient may select one of the icons 752-766. If the recipient selects any of the icons other than the Too Loud 752 or Maximum Acceptable Loudness 754 icon, the current level of the applied stimulation may be increased. This current level may be increased by a specified step size such as discussed above with reference to FIG. 7A. Further, this step size may be different depending on which icon is selected by the recipient. For example, if the recipient selects an icon indicating that they perceived no sound 766, the current level may be increased by a larger step size that if the recipient selected the icon labeled Loud 756.

As one example, the step sizes for the icons may be set such that the Loud icon 756 increases the current level by 1 step, the Between Medium and Loud icon 758 increases the current level by 2 steps, the Medium icon 760 increases the current level by 3 steps, the Between Soft Medium icon 762 increases the current level by 4 steps, the Soft icon 764 increases the current level by 5 steps, and the No Sound icon 766 increases the current level by 6 steps.

If the recipient selects the Too Loud icon 752, the current level may be reduced by a specified step size (e.g., 2 steps). And, if the recipient select the Maximum Acceptable Loudness icon 754, the fitting system may determine that the maximum comfort level for the recipient for this electrode and Rate×Max combination is equal to the current level of the applied stimulation.

GUI 750 also includes an icon labeled play 770. The user may select the play icon 770 to begin the process of measuring the maximum comfort levels for the recipient. After the user selects the play icon 770, the icon may replaced with an icon labeled stop that a recipient may use to terminate the process, such as discussed above with reference to the stop icon 712 of GUI 700.

Figure 8:
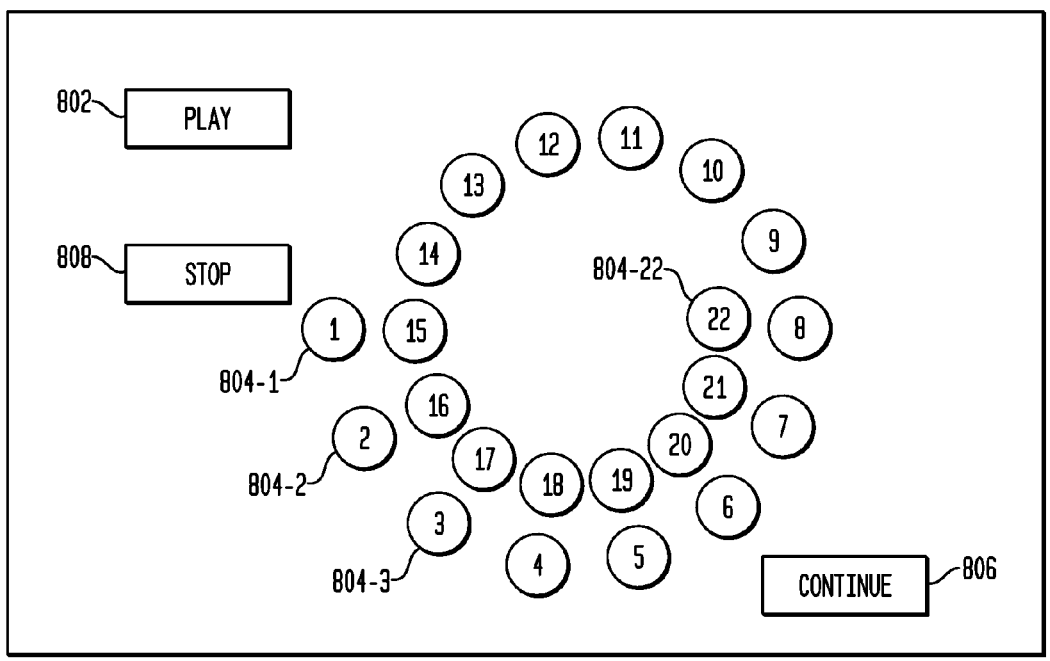
FIG. 8 provides an exemplary GUI that may be used by a recipient to individually adjust electrode current levels, in accordance with an embodiment.

Fitting function 304 may also be used to identify individual electrodes that are either too loud or too soft, compared to other electrodes. FIG. 8 provides an exemplary GUI 800 that may be used to individually adjust electrode current levels, in accordance with an embodiment. Fitting function 304 may provide this GUI 800 to the recipient after determining the threshold and comfort levels. For ease of explanation, GUI 800 will be referred to as a Sweep GUI 800. As illustrated, Sweep GUI 800 may provide an icon 804-1 through 804-22 corresponding to each electrode of the electrode array of cochlear implant 100. Sweep GUI 800 may further comprise a play button 802, a continue button 806, and a stop button 808.

The play button 802 may be used to direct fitting function 304 to sweep through (e.g., sequentially) all or a subset of all electrodes at a particular current level, such as for example, the measured comfort level for the electrode, or a particular number of step sizes below the comfort level. As each electrode is played (i.e., stimulation applied via the electrode) the electrode being stimulated may be highlighted on the GUI 800. This may be accomplished, for example, by changing the color of the icon, changing its size or shape, a combination thereof, or any other mechanism. Electrodes identified by the recipient as too loud or too soft, in relation to their neighbors, may be selected by the recipient clicking-on the icon 604 corresponding to the electrode. The fitting function 304 may then change the color of the selected icon to a particular color (e.g., red), or its size, shape, a combination thereof or another mechanism may be used to highlight the selection of the electrode. The recipient may select the continue button 806 to advance to a balancing GUI that may be used to balance the current level of the selected electrode. The stop button 808 may be used to stop the process.

Figure 9:
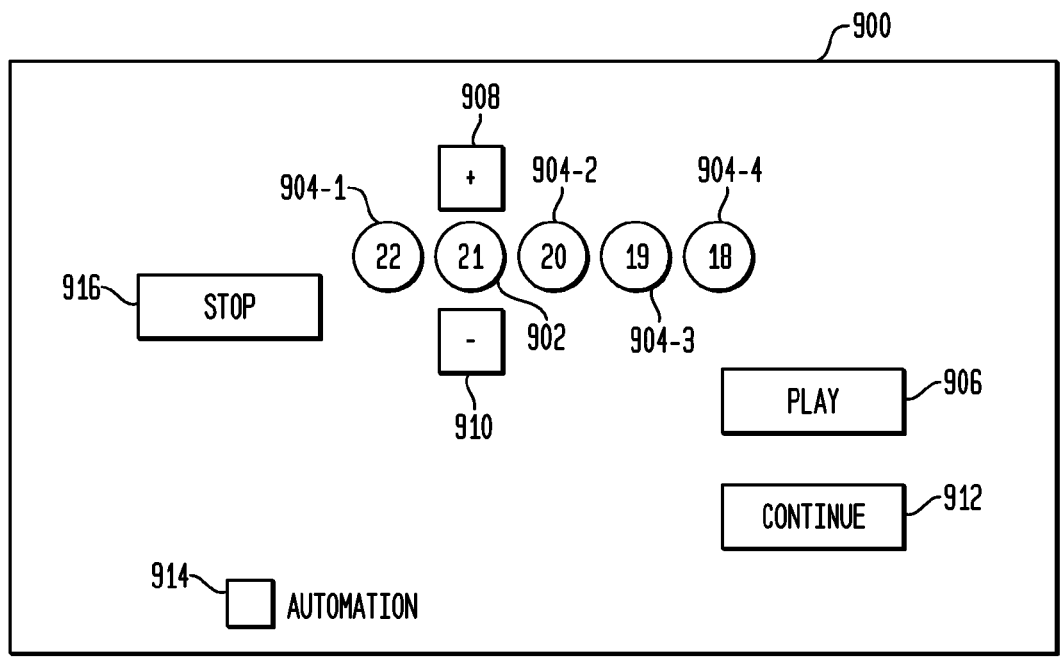
FIG. 9 illustrates an exemplary GUI that may be used by a recipient for balancing an electrode, in accordance with an embodiment.

FIG. 9 illustrates an exemplary GUI 900 that may be used for balancing an electrode, in accordance with an embodiment. Balancing GUI 900 may be used, for example, by a recipient to set all electrodes to the same loudness level. GUI 900 displays an icon 902 representative of the electrode identified by the recipient using sweep GUI 800 as either too loud or too soft. The selected electrode icon 902 is situated among a number, for example four, other electrode icons 904-1 through 904-4 representative of electrodes that were not identified. These other electrodes may be selected so that some, for example two, are below the selected electrode and some, for example two, are above the selected electrode. If, however, there is only one electrode above or below the selected electrode, then only that electrode may appear above or below the selected electrode. Or, if there are no electrodes above or below, then only electrodes from the side in which there are electrodes may be used.

In the exemplary GUI 900, only one icon 904-1 is illustrated to the left of icon 902 and three icons 904-2 thru 4 are illustrated to the right of icon 902. GUI 900 also illustrates a Play button 906 that causes fitting function 304 to sequentially apply stimulation on each of the electrodes corresponding to the displayed icons 902 and 904. The Louder button 908 may be selected by the recipient to increase the level (T, C, or both) of the selected electrode by a small level increment (e.g., one step), process the audio with the new levels, and then present the five electrodes sequentially. The Softer button 910 may be selected by the recipient to decrease the level (T, C, or both) of the selected electrode by a small level increment (e.g., one step), process the audio with the new levels, and then present the five electrodes sequentially. The Continue button 912 may be selected by the recipient to progress to a screen for balancing the next selected electrode, if one exists. Otherwise, it initiates the next command in the automation protocol if, for example, the "Automation checkbox" 914 is checked. If automation is not currently selected (the "Automation checkbox" 914 is not checked), the task/graphics screen is emptied. GUI 900 may also comprise a Stop button 916 to terminate the procedure.

As noted above, in embodiments, the parameter setup functional block 302 may permit a clinician to specify the type of measurements to be conducted during the fitting session as well as the parameters for these measurements. These parameters (e.g., instructions) may be created using, for example, a clinical GUI or, for example, created using a simple text editor displayed on clinician console 240. These parameters may include, for example, the electrodes to use during the measurements, the number of reversals used by the fitting system in obtaining the levels using psychophysical measurements, the increment and decrement step sizes, the duration of the applied stimulation, etc. After specifying the parameters, the parameters may be included in a file stored by fitting system controller 212. Exemplary clinical GUIs will be discussed in more detail below with reference to FIGS. 10A and 10B.

FIGS. 10A and 10B illustrates an exemplary clinical graphical user interface 800 that may used to add a MAP for level (e.g., T and C) measurement, in accordance with an embodiment. As illustrated, interface GUI 1000 may comprise a portion 1002 for adding a MAP, and a portion 1040 for listing MAPs already created and stored by fitting system controller 212, such as, for example, in a MAP database. The portion for adding MAPs 1002 may comprise a tab 1001 for creating new MAPs, and a tab 1003 for searching for existing MAPs. FIG. 10A illustrates clinical interface 1000 when tab 1001 is selected. As illustrated, when tab 1001 is selected, portion 1002 may comprise pull-down 1012 for specifying the stimulation for the new MAP, a pull-down 1014 for specifying the number of maxima for the new MAP, and a checkbox 1016 for selecting whether Adaptive Dynamic Range Optimization (ADRO) should be enabled or not for the new MAP. Additionally, portion 1002 may comprise an add MAP button 1018 for directing the fitting system to add the MAP with the specified stimulation rate and number of maxima to the MAP database. When the clinician or audiologist presses the add MAP button 1018, the MAP is first added to block 819 which lists the MAPs that the fitting system is to create. Portion 1002 may also include a remove MAP button 1020 for deleting MAPs from block 1019.

Portion 1004 may list each of the previously created MAPs, as well as a check box 1024 corresponding to each listed MAP. The clinician or audiologist may check the corresponding checkbox 1024 for each MAP for which the fitting system 206 is to obtain the levels. Interface 1000 may also comprise a Go button 1030 that the clinician or audiologist may select to instruct the fitting system to obtain the levels for the MAPs created in block 1019 as well as those in portion 1004 in which the corresponding checkbox 1024 is checked. In response to selection of Go button 1030, fitting system controller may create and store an instruction set that may be used for measuring the stimulation level parameters for the specified Maps.

FIG. 10B illustrates clinical interface 1000 when tab 1003 is selected. As illustrated, when tab 1003 is selected, portion 1002 includes a box 1050 permitting the clinician or audiologist to enter, for example, a location for a file including the MAPs that are to be searched. Portion 1002 may also include a browse button 1054 that the clinician may press to locate such a file. This browse button 1054 may function in a similar manner to browse buttons commonly used in computer based systems. These MAPs may then be displayed in block 1056. When Go button 1030 is selected, fitting system 1006 may create an instruction set for obtaining the levels from the MAPs identified in block 1056 as well as any in portion 1004 in which the corresponding checkbox 1024 is checked. This instruction set may be used by the fitting system for obtaining the levels, such as was discussed above with reference to FIG. 5. Or, for example, the information specifying the MAPs may be saved and used, for example, to create an instruction set after other parameters are specified.

It should be noted that GUIs 1000 is exemplary only and provided to illustrate one example of a clinical interface that may be used to specify the parameters for the measurements to be performed in obtaining the stimulation level parameters (e.g., T or C levels). And, other user interfaces may be used. For example, the buttons, pull-downs, etc. may be organized in a different manner, or different buttons, etc. may be used, without departing from the invention.

Figure 11:
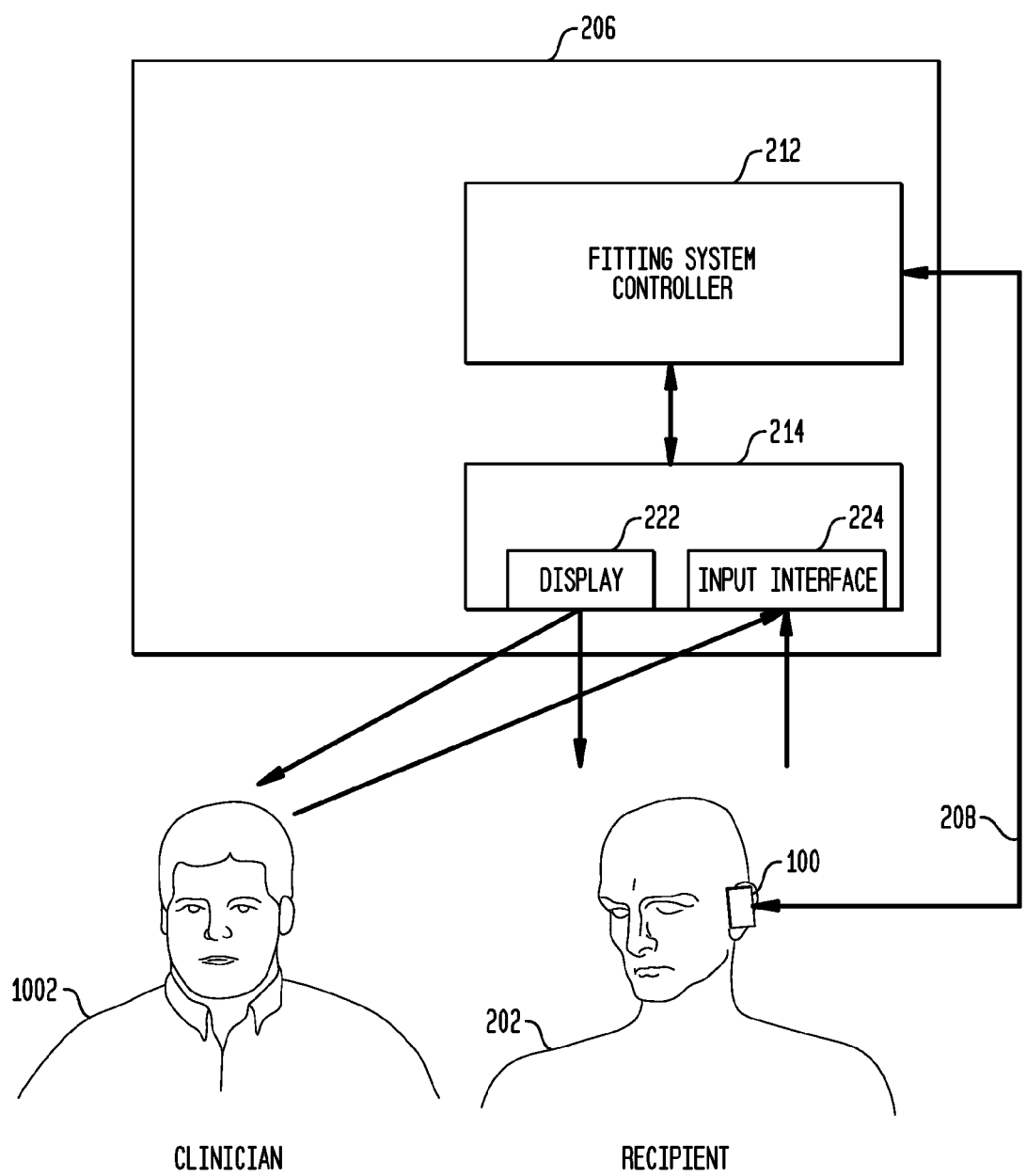
FIG. 11 illustrates a fitting system in which the clinician directly accesses the fitting system, in accordance with an embodiment of the invention.

As noted above, in the embodiment of FIG. 2, the clinician may access the fitting system 206 remotely via a network 250. However, in an embodiment, rather than remotely accessing the fitting system, the clinician may access the fitting system 206 directly. FIG. 11 illustrates a fitting system in which the clinician directly accesses the fitting system, in accordance with an embodiment of the invention. As shown, in this exemplary system 1100, the clinician 1102 accesses the fitting system 206 using the same display 214 and input interface 224 used by recipient 202. In such an embodiment, the fitting system 206 need not be connected to or be capable of connection to network 250. In another embodiment the fitting system 206 may include, for example, a separate display and input interface for use by the clinician.

Figure 12:
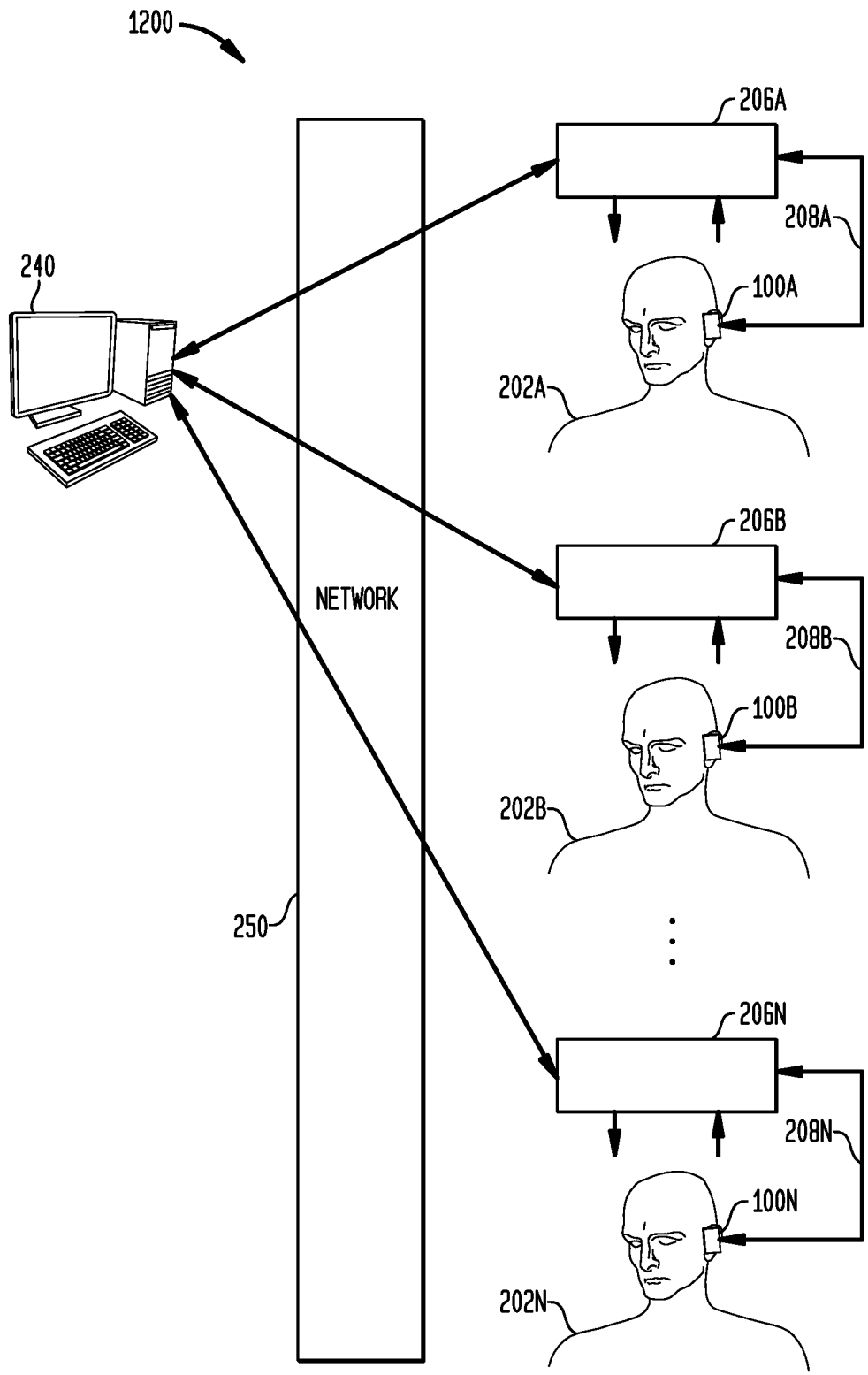
FIG. 12 provides an exemplary illustration of a system in which a clinician console 240 remotely connected to a plurality of fitting systems.

As noted above, embodiments of the present invention enable a clinician to oversee a plurality of recipient fitting sessions that may be occurring simultaneously. FIG. 12 provides an exemplary illustration of a system 1200 in which a clinician console 240 remotely connected to a plurality of fitting system's 206A-206N. Using such a system a single clinician may oversee the recipient driven fitting sessions performed by fitting system's 206A-206N. Such a system may operate in accordance with the above described systems and procedures.

It should be noted that although the above-discussed embodiments were discussed with reference to a cochlear implant, in other embodiments a fitting system may be used to permit a recipient to measure the stimulation level parameters of other stimulating medical devices, such as, for example, bone conduction devices, auditory brain stimulators, etc.

Various implementations of the subject matter described, such as the embodiment of FIGS. 2,3, components of may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device These computer programs (also known as programs, software, software applications, applications, components, or code) include machine instructions for a programmable processor, and may be implemented in a high-level procedural and/or object-oriented programming language, and/or in assembly/machine language. As used herein, the term "machine-readable medium" refers to any computer program product, computer-readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. Similarly, systems are also described herein that may include a processor and a memory coupled to the processor. The memory may include one or more programs that cause the processor to perform one or more of the operations described herein.

All documents, patents, journal articles and other materials cited in the present application are hereby incorporated by reference.

Embodiments of the present invention have been described with reference to several aspects of the present invention. It would be appreciated that embodiments described in the context of one aspect may be used in other aspects without departing from the scope of the present invention.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart there from.

What is claimed is:

1. A system for fitting a stimulating medical device to a recipient, comprising:
    a fitting system controller configured to:
        transmit a signal to cause the stimulating medical device to apply stimulation to the recipient; and
        pass control from a clinician to the recipient;
    a display configured to display a graphical user interface to the recipient; and
    an input device configured to receive a response from the recipient, using the graphical user interface, regarding stimulation applied by the stimulating medical device;
    wherein the fitting system controller is further configured to:
        pass control from the recipient to the clinician;
        determine a value for a set of at least one device parameter using the received response;
        present the determined set of parameter values to a clinician; and
        receive an indication from the clinician that the determined set of parameter values is approved.

2. The system of claim 1, wherein the fitting system controller is further configured to:
    receive authentication information from the clinician;
    authenticate the clinician by determining if the received authentication information matches stored authentication information for the clinician; and
    store the determined set of device parameter values, if approved by said clinician and said clinician is authenticated.

3. The system of claim 2, wherein the fitting system further comprises:
    a stimulating medical device interface configured to provide the determined set of device parameter values to the stimulating medical device such that the stimulating medical device stores the device parameter values for subsequent use by the stimulating medical device in applying stimulation to the recipient.

4. The system of claim 1 wherein:
The fitting system controller is further configured to:
   Pass control initially to the clinician; and
The system further comprises:
   A clinician console configured to display a clinician interface to the clinician and receive, from a clinician via the clinician interface, a value for at least one fitting parameter for use in fitting the stimulating medical device to the recipient, and provide the at least one fitting system parameter to the fitting system controller.

5. The system of claim 4, wherein the clinician console is connected to the fitting system controller via a network.

6. The system of claim 5,
wherein the network comprises the Internet.

7. The system of claim 4, wherein the fitting session controller is further configured to receive authentication information from the clinician after the fitting parameters are provided and commence determining the set of one or more device parameter values for the stimulating medical device after the clinician is authenticated.

8. The system of claim 4, wherein the at least one fitting parameter comprises at least one parameter selected from the set of: a number of reversals; a number of beeps; a sound source; a stimulation rate; a number of maxima, and an interpolation algorithm.

9. The system of claim 1, wherein the graphical user interface comprises a plurality of icons, each icon corresponding to a particular perception by the recipient regarding the applied stimulation; and
   wherein the fitting system controller is further configured to receive an indication that the recipient selected a particular icon displayed by the graphical user interface.

10. The system of claim 1, wherein the set of one or more device parameters comprises one or more of a threshold for a stimulation channel, and a maximum comfort level for the stimulation channel.

11. The system of claim 1, wherein the fitting system controller is further configured execute a genetic algorithm to select the value(s) for the set of one or more device parameters, wherein the genetic algorithm is operable to generate one or more successive generations of values for the device parameter(s).

12. A system for fitting a stimulating medical device to a recipient, comprising:
   recipient-driven fitting means for passing control from a clinician to the recipient and for executing a recipient driven fitting session for determining values for a set of one or more device parameters for the stimulating medical device;
   presentation means for passing control from the recipient to the clinician and for presenting the determined set of parameter values to a clinician; and
   approval means for receiving an indication from the clinician that the determined set of parameter values are approved.

13. The system of claim 12, further comprising:
   clinician-input means for receiving authentication information from the clinician;
   authentication means for authenticating the clinician by determining if the received authentication information matches stored authentication information for the clinician; and
   means for storing the determined set of device parameter values, if approved by said clinician and said clinician is authenticated.

14. The system of claim 12, wherein:
   the presentation means is further configured for passing control initially to the clinician and for displaying a clinician interface to the clinician;
   the clinician-input means is further configured for receiving, from the clinician via the clinician interface, at least one value of at least one fitting parameter for use in fitting the stimulating medical device to the recipient; and
   the recipient-driven fitting means is further configured for using the at least one value of the at least one fitting parameter to determine the set of one or more device parameters for the stimulating medical device.

15. The system of claim 14, wherein:
   the clinician-input means is further configured for receiving the at least one value of the at least one fitting parameter from the clinician via a network.

16. The system of claim 15, wherein:
   the network comprises the Internet.

17. The system of claim 14, wherein:
   the clinician-input means is further configured for receiving authentication information from the clinician after receiving the value for the at least one fitting parameter; and
   the recipient-driven fitting means is further configured for commencing the determination of the set of one or more device parameter values for the stimulating medical device after receiving the value for the at least one fitting parameter if the clinician is authenticated by the authentication means.

18. The system of claim 14, wherein the at least one value for the at least one fitting parameter received via the clinician-input means comprises:
   a value for at least one parameter selected from the set of:
   a number of reversals;
   a number of beeps;
   a sound source;
   a stimulation rate;
   a number of maxima; and
   an interpolation algorithm.

19. The system of claim 12, wherein the determined set of one or more device parameters comprises one or more of a threshold for a stimulation channel, and a maximum comfort level for the stimulation channel.

20. The system of claim 12, wherein:
   the recipient-driven fitting means is further configured for executing a genetic algorithm to select the value(s) for the set of one or more device parameters, the genetic algorithm being executable to generate one or more successive generations of values for the device parameter(s).

21. A system for fitting a stimulating medical device to a recipient, comprising:
   a recipient interface configured to exchange information with the recipient;
   a clinician interface configured to exchange information with the clinician; and
   a fitting system controller configured to:
      control the stimulating medical device to apply stimulation to the recipient;
      pass control from the clinician to the recipient;
      conduct a recipient-driven session using the recipient interface for determining at least one value for a set of at least one device parameter based on one or more instances of feedback from the recipient responsive to one or more instances of stimulation applied to the recipient;

pass control from the recipient to the clinician; and conduct, subsequently to the recipient-driven session, a clinician-driven session using the clinician interface for:

presenting the determined set to the clinician; and receiving approval for the determined set from the clinician.

22. The system of claim 21, wherein the fitting system controller is further configured to:

store the determined set if approved by the clinician.

23. The system of claim 22, wherein the fitting system controller is further configured to:

authenticate the clinician after the approval is received; and store the approved determined set if the clinician is successfully authenticated.

24. The system of claim 23, wherein the fitting system controller is further configured to:

receive, after the approval is received, credential information from the clinician; and compare the received credential information against stored credential information for the clinician.

25. The system of claim 21, wherein the fitting system controller is further configured to:

pass control initially to the clinician;

conduct, before the recipient-driven session, an initializing clinician-driven session using the clinician interface for receiving, from the clinician at least one value of at least one fitting parameter; and determine, during the recipient-driven fitting session, the set of at least one value of at least one device parameter based on the at least one value of the at least one fitting parameter.

26. The system of claim 25, wherein the fitting system controller is further configured to:

authenticate, after the at least one value of the at least one fitting parameter is received, credential information from the clinician; and conduct the subsequent recipient-driven session if the clinician is successfully authenticated.

27. A system for fitting a stimulating medical device to a recipient, comprising:

a recipient interface configured to exchange information with the recipient;

a clinician interface configured to exchange information with the clinician; and a fitting system controller configured to:

control the stimulating medical device to apply stimulation to the recipient;

conduct a recipient-driven session using the recipient interface for determining at least one value for a set of at least one device parameter based on one or more instances of feedback from the recipient responsive to one or more instances of stimulation applied to the recipient; and conduct, subsequently to the recipient-driven session, a clinician-driven session using the clinician interface for:

presenting the determined set to the clinician; and receiving approval for the determined set from the clinician; and store the determined set if approved by the clinician; and wherein:

the recipient-driven session is a first recipient-driven session; and the fitting system controller is further configured to conduct at least a second recipient-driven sessions concurrently with the first recipient-driven session.

* * * * *